(12) United States Patent
Martin

(10) Patent No.: US 6,480,793 B1
(45) Date of Patent: Nov. 12, 2002

(54) FLOW CONDITION MONITOR

(75) Inventor: Clifford B. Martin, Somers, CT (US)

(73) Assignee: Westinghouse Electric Company LCL, Pittsburgh, PA (US)

( * ) Notice: Subject to any disclaimer, the term of this patent is extended or adjusted under 35 U.S.C. 154(b) by 96 days.

(21) Appl. No.: 09/697,725

(22) Filed: Oct. 27, 2000

(51) Int. Cl.[7] .................. G01F 1/00; G06F 19/00
(52) U.S. Cl. ............... 702/45; 702/50; 702/100; 73/861.18
(58) Field of Search .............. 702/40, 43, 45, 702/50–51, 54–55, 100, 104; 73/861.18, 861.19, 861.2, 861.23, 861.25; 376/246, 249, 258

(56) References Cited

U.S. PATENT DOCUMENTS

| 4,908,775 A | * | 3/1990 | Palusamy et al. ............ 702/34 |
| 4,948,552 A | | 8/1990 | Mollot ....................... 376/246 |
| 5,096,657 A | | 3/1992 | Merciez ...................... 376/247 |
| 5,131,278 A | | 7/1992 | Baumoel ................... 73/861.18 |
| 5,157,619 A | * | 10/1992 | Palusamy et al. ............ 702/43 |
| 5,176,631 A | | 1/1993 | Koenig ........................ 604/65 |
| 5,396,524 A | | 3/1995 | Lyman ....................... 376/246 |
| 5,463,905 A | | 11/1995 | Baird ....................... 73/861.25 |
| 5,503,035 A | | 4/1996 | Itoh et al. ................ 73/861.23 |
| 5,533,074 A | * | 7/1996 | Mansell ...................... 376/258 |
| 5,633,809 A | | 5/1997 | Wissenbach ................ 364/510 |
| 5,639,667 A | | 6/1997 | Heslot ........................ 436/148 |
| 5,673,026 A | | 9/1997 | Marrelli et al. ............. 340/608 |
| 5,728,947 A | | 3/1998 | Marsh et al. ............. 73/861.28 |
| 5,861,560 A | * | 1/1999 | Harvey ..................... 73/861.19 |
| 5,881,117 A | | 3/1999 | Matteson .................... 376/258 |

* cited by examiner

Primary Examiner—Bryan Bui (57) ABSTRACT

A system and method of detecting and monitoring flow conditions in the coolant of a nuclear reactor that relies upon acoustic or optical differences in the various flow conditions. The system uses a database of acoustic or optical characteristics of the various known flow conditions being monitored, and a processor that compares the detected acoustic signals with the known acoustic characteristics. The processor uses various methods of discrimination, such as altering or decaying the transmitted signal, to aid in the interpretation and comparison of the signals. The acoustic detection is provided by a pair of sensor assemblies positioned a distance from each other to detect variations in the acoustic patterns associated with the coolant flow. A transmitter and receiver of each sensor assembly can be positioned on opposite sides of the pipe in which the coolant is flowing, or on the same side of the pipe, depending upon which configuration provides the best discrimination between the flow conditions being monitored. The monitoring system is effective for determining, among other things, the existence of bubbles entrained in the coolant, the existence and level of a free surface, the existence of vortex or whirlpool formations, and the existence of entrained solid particulates.

25 Claims, 7 Drawing Sheets

FLOW CONDITION MONITOR

BACKGROUND OF THE INVENTION

1. Field of the Invention

The present invention relates generally to flow condition monitoring systems and methods. In particular, the present invention relates to a system and method for monitoring flow conditions in the coolant and other fluids circulating through a nuclear power plant.

2. Description of the Related Art

In a nuclear plant of the pressurized water reactor (PWR) type, coolant fluid, which is basically boron and water, is continuously transferred through a closed circulation loop between a nuclear reactor and one or more steam generators.

During power production, the pressurized coolant absorbs heat released by the thermonuclear reaction occurring in the reactor. The heated coolant then flows through a main pipe which is appropriately known as the "hot leg" of the circulation loop. The hot leg delivers the hot coolant to a steam generator.

In the steam generator, the coolant fluid circulates through a heat exchanger. The heat exchanger cools the coolant fluid and uses the heat removed from the coolant to produce steam. This steam is eventually used to drive turbines and generate electricity.

After the circulating coolant is cooled by a heat exchanger, a circulation pump removes the coolant from the steam generator via a "suction leg" and returns it to the reactor via a "cold leg" and inlet. The coolant is then reheated in the reactor and the cycle repeats.

This circulation of coolant through one or more loops is critical for the operation of the power plant. Not only does it deliver heat energy to the steam generators where the energy is used to produce steam for driving the turbines, but the circulating coolant also prevents the reactor core in the reactor from overheating.

Nuclear power plant systems, including the steam generators, require periodic maintenance. In particular, the fluid circulation system must be inspected for potential degradation, and nozzle dams must be installed and removed from the steam generators to allow inspection and maintenance to be performed in a dry environment.

In order to install and remove nozzle dams, the coolant fluid must be drained from the steam generator. This requires lowering the fluid level in the main circulation loop and consequently the hot leg or main pipe. During such a maintenance period, which is termed a "shutdown," the coolant continues to be heated by decay heat from the reactor core and is cooled by an alternate heat exchanger and auxiliary circulatory system known as the "shutdown cooling system."

In order to lower the coolant or water level in the shutdown reactor system to permit refueling of the reactor core and to allow maintenance operations on portions of the system above the lowered water level, the water level must be controlled and maintained at a minimum level and flow rate to continuously provide adequate core cooling. This minimum level is about midway within the reactor coolant system main loop piping (the hot leg) and is commonly referred to as "midloop."

During midloop operation, coolant water is circulated through the system to cool the core. Typically, there are a drain line or lines which communicate with the lower region of one or more of the main loop pipes or legs to draw the heated water from the core for cooling by the alternate heat exchanger in the shutdown cooling system and subsequent recirculation of cooled water to a reactor inlet and thus to the core.

It is possible to experience the formation of a Coriolis effect vortex in the drain line during midloop operation if the water level is lowered too far down or if the drain flow rate is too high. Such a vortex is undesirable because it limits the rate at which coolant flow can be drained from the system, and it can eventually lead to cavitations in the drain pump. Both results cause concern for continued cooling of the core.

The current methods to avoid vortex formation rely on keeping the water level as high as possible and/or reducing the flow rate, resulting in a conflict between the need to lower the water level for maintenance service, and the need to keep the water level high and at a sufficient rate for safe core cooling. Midloop measuring systems in use are related to a detection of the water elevation and inference of the status of the vortex therefrom.

In nuclear power plants much attention has been given to shutdown cooling system reliability, especially during reactor coolant system midloop water level operation. Midloop operation in a typical pressurized water reactor (PWR) nuclear steam supply system, for example, for the installation and removal of steam generator nozzle dams, can be a very difficult operational process. In fact, typically, the water level allowed tolerance is approximately plus or minus one inch (+/−1"). A vortex detection system has been disclosed in U.S. Pat. No. 5,861,560 by Robert P. Harvey to detect air vortexing and cavitation and thereby improve the shutdown cooling system reliability. However, the vortex detection system of Harvey is limited in its capability and usefulness because it relies only on the disruption of the signal of a conventional ultrasonic flowmeter to trigger an alarm indicating a vortex condition. The vortex detection system of Harvey is not capable or suitable for detecting various other fluid flow conditions throughout the nuclear reactor, such as fluid levels, entrained solid particulates caused by accident scenarios, condensible and noncondensible bubbles entrained in the fluid, and so forth. The vortex detection system of Harvey uses only one sensor and is looking only for the vortex condition in the drain pipe.

SUMMARY OF THE INVENTION

The present invention provides a flow condition monitor system and method for a nuclear reactor that rely upon acoustic detection of various flow conditions, including the existence of condensible or noncondensible bubbles entrained in the fluid, the existence and level of a free surface, the existence of vortex or whirlpool formations, the existence of entrained solid particulates, and various other flow conditions. The system uses a database of the acoustic characteristics of known flow conditions, and a processor that compares the detected acoustic signals with the known characteristics of the various flow conditions being monitored. The processor uses various means of discrimination, such as altering or decaying the transmitted signal, to aid in the interpretation, comparison and identification of the flow conditions.

The acoustic detection is provided by at least one sensor, and preferably a plurality of sensors, positioned to receive acoustic signals from the fluid flow being monitored. The sensor or sensors can be passive acoustic sensors, such as sensitive microphones or accelerometers attached to the pipe. Alternatively, the sensors can be ultrasonic devices that include ultrasonic transmitters and receivers positioned to capture variations associated with the coolant flow. In still another alternative, the sensors can be laser devices that include a laser source and a laser receiver diametrically opposed on a pipe structure whereby variations associated with the coolant flow cause unique disruptions in the laser signal.

In one embodiment, a first sensor is positioned upstream from a second sensor a sufficient distance that attenuations in the signal and noise detected by the first sensor can be detected by the second sensor. The signals can then be processed and compared with the acoustic characteristics of known flow conditions to determine the flow condition being detected. The transmitter and receiver of the sensors can be positioned on opposite sides of the pipe in which the coolant is flowing, or on the same side of the pipe, depending on the particular conditions and location of the fluid flow being monitored. An arrangement of the transmitter and receiver on opposite sides of the pipe will allow the compressibility difference of the water and air at the air/water interface to be taken into account, while an arrangement of the transmitter and receiver on the same side of the pipe will capture the variation associated with the reflection from the interface. Various arrangements of the sensors are described below and are shown in the accompanying drawings.

According to a broad aspect of the present invention, a flow condition monitoring system is provided for monitoring fluid flow conditions in a nuclear power plant. The system includes: a first sensor assembly positioned near a fluid flow to be monitored, said sensor assembly having an output signal; a database containing known characteristics of various fluid flow conditions being monitored; and a processor means connected to said first sensor assembly and to said database for receiving and comparing the signal from the sensor assembly with the known characteristics contained in the database to determine a condition of the fluid flow.

BRIEF DESCRIPTION OF THE DRAWINGS

The present invention will become more clearly appreciated as the disclosure of the invention is made with reference to the accompanying drawings. In the drawings.

DETAILED DESCRIPTION OF THE INVENTION

Figure 1:
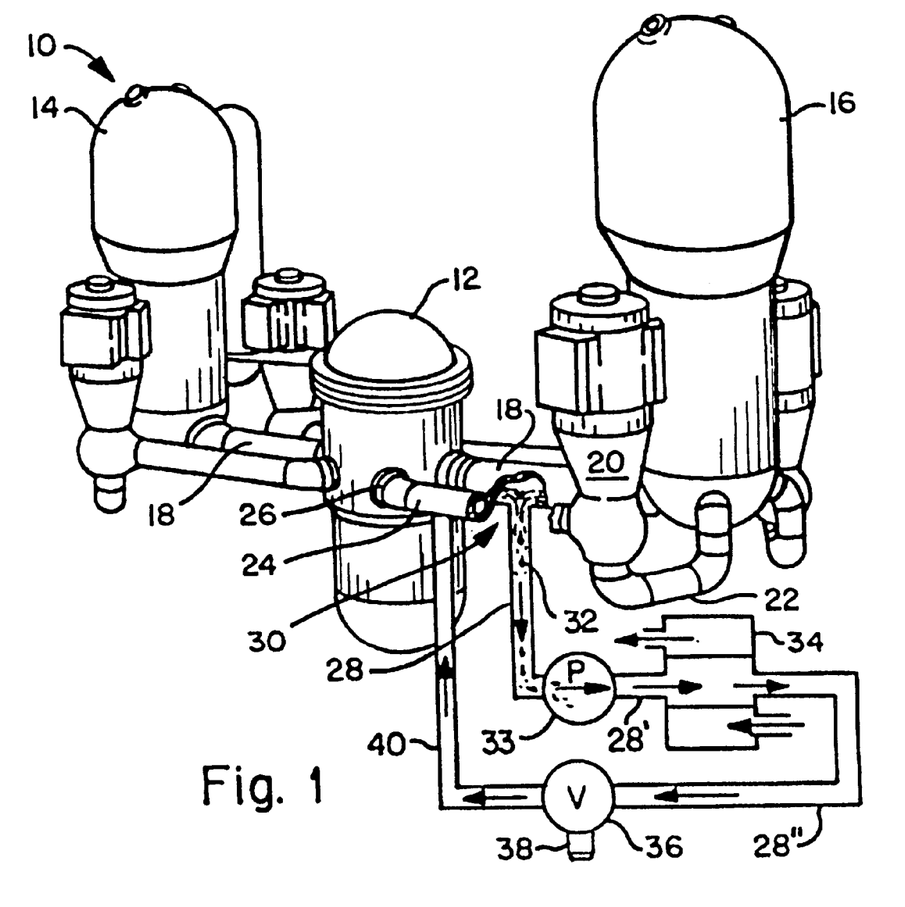
FIG. 1 is a schematic drawing of a nuclear power plant having two steam generators with a shutdown cooling system and drain illustrated in connection with one of the steam generators.

FIG. 1 illustrates a nuclear power plant incorporating the present invention. The numeral 10 generally designates a pressurized water reactor type of plant in which water is continuously transferred through a closed circulation loop between a reactor 12 and each of two steam generators 14 and 16, respectively.

The water coolant from the reactor 12 flows through main pipes or hot legs 18 to the respective steam generators 14 and 16, each of which has similar piping.

In the case of the steam generator 16, for illustration, a coolant system circulation pump 20 circulates water, which has been cooled in the steam generator, through a suction leg pipe 22, and back to the reactor 12 via a cold leg 24 and an inlet 26. The shutdown cooling system drain pipe 28 intersects the lower region of the substantially horizontal main pipe or hot leg 18. Within the lower region of the main pipe 18 is a vortex 30.

Flow from the main pipe 18 into the drain pipe 28 forms the vortex 30 which creates cavitations in a drain pump 33 which has direct fluid communication from the main pipe 18 where it intersects with the lower region of the main pipe 18. This vortex 30 inhibits the flow rate in the drain pipe 28 and the drain pump 33 by creating voids and cavitation 32. The drain pump 33 discharges through a conduit 28' to an auxiliary heat exchanger 34 downstream from the drain pump 33 for performance of the shutdown cooling system water cooling function.

From the heat exchanger 34 the water is directed by a valve 36 in a drain pipe section 28" to a drain 38 or to a section of pipe 40 which is connected to the main pipe cold leg 24 for recirculation through the inlet 26 of the reactor 12 to cool the core during the shutdown period or in an emergency when the auxiliary heat exchanger's capacity is needed for safety reasons.

Figure 2:
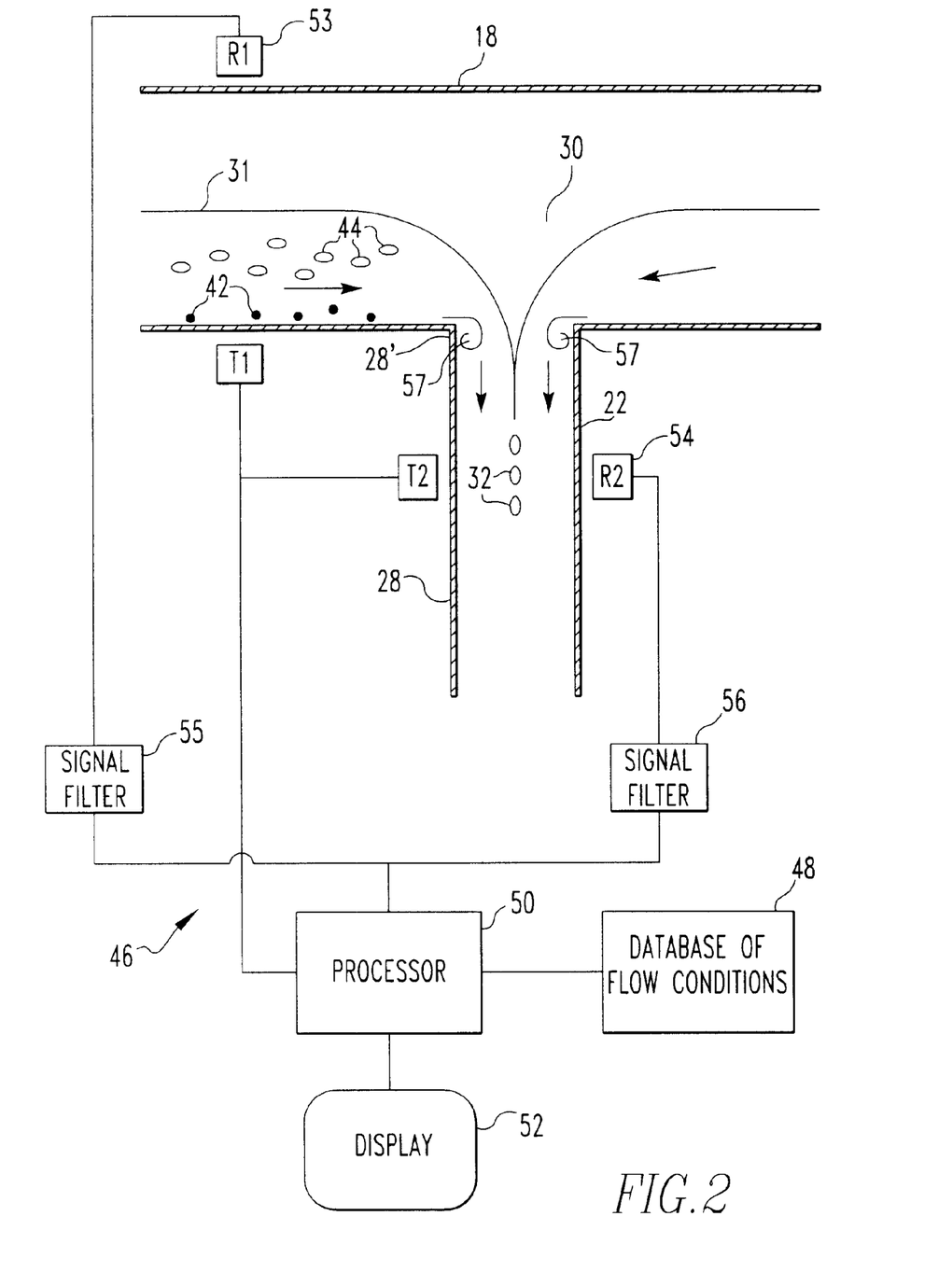
FIG. 2 is an enlarged, fragmented schematic view of the hot leg and drain pipe of FIG. 1 with a flow condition monitoring system according to an embodiment of the present invention attached.

In FIG. 2, the enlarged vortex 30 is illustrated at the junction of the main pipe 18 and the drain pipe 28. A typical level of coolant in main pipe 18 for midloop operation is designated by the numeral 31. Entrained air from the vortex 30 creates voids and cavitation 32 in the drain pipe 28 and the pump 33. Also shown in the fluid flow in FIG. 2 are entrained solid particulates 42 and entrained bubbles 44, both of which can provide important indications of the operating conditions of the nuclear power plant 10. The solid particulates 42 may include, for example, sand, metal flakes, dust particles, crystalline particles, and so forth, each of which has different acoustic characteristics as they bounce off one another or off the pipe wall. The entrained bubbles 44 may include noncondensible bubbles, such as air, helium or hydrogen, or condensible bubbles, such as steam vapor bubbles, each of which has different frequency variations and acoustic characteristics.

The flow condition monitor of the present invention uses acoustic or optical/laser detection equipment to search for and monitor various conditions of the coolant flow, including the existence of condensible or noncondensible bubbles 44 entrained in the coolant, the existence and level of a free surface 31, the existence of vortex or whirlpool formations 30, the existence of entrained solid particulate 42, and various other conditions that affect the nuclear reactor.

The flow condition monitor 46 according to one embodiment of the present invention is shown in FIG. 2. The flow condition monitor 46 includes a database containing a library of the predetermined acoustic characteristics of the various conditions to be monitored. The library is developed by simulating the various flow conditions and combinations of flow conditions that may arise in the nuclear power plant 10, and recording the acoustic patterns that emanate from such flow conditions. A main processor 50 compares and matches signals from the acoustic detection equipment with the acoustic patterns of the known possible flow conditions contained in the database 48. When the detected acoustic characteristics are matched with a predetermined characteristic, the detected flow conditions are communicated to the nuclear plant operator using a video display 52, an audio signal, or other suitable communication means.

The acoustic measurements in the monitor 46 shown in FIG. 2 are obtained by first and second acoustic sensor assemblies 53, 54 each having a respective transmitter T1, T2 and receiver R1, R2 positioned near the coolant flow. The first sensor assembly 53 includes an ultrasonic transmitter T1 and receiver R1 positioned near the main pipe 18 at a location upstream of the drain pipe 28. The second sensor assembly 54 includes an ultrasonic transmitter T2 and receiver R2 positioned near the drain pipe 28 downstream of the top opening 28' of the drain pipe 28. The acoustic signals detected by the receivers R1, R2 are filtered by suitable signal filters 55, 56 to remove unwanted noise, and are then inputted to the main processor 50.

Although there is a possibility that many or all flow conditions being monitored in the nuclear power plant 10 could exist simultaneously, that possibility is remote. More likely is a combination of the flow conditions that can be anticipated in advance and simulated to provide a corresponding acoustic pattern to be stored in the database 48 for such combination of flow conditions. Since the acoustic signals from the various flow conditions are sometimes similar in amplitude and frequency, other means of discrimination, such as the alteration or decay of the transmitted signal, can be implemented by the processor 50 to aid in the interpretation.

Since sound is associated with density and pressure fluctuation, a steady, low Reynolds number flow, such as a laminar flow, may not generate sound. Turbulence or some other periodic or vibratory excitation, such as vortex shedding downstream of an obstacle in the example laminar flow field, might be necessary in some cases to generate acoustic patterns or signatures that may be detected.

Acoustic emission from noncondensible bubbles requires an excitation. This excitation may be a consequence of the generation of the bubbles or a pressure disturbance caused by an obstacle in the flow field or eddies or turbulence in the coolant flow. For the ideal case of a Rayleigh bubble, the frequency of the resulting oscillation, which may be perceived as an acoustic propagation through the fluid, may be expressed by a simple relationship of the undisturbed size of the bubble, the density and distant pressure of the coolant, the specific heats of the noncondensible gas, and the acceleration of gravity. For a condensible bubble, the frequency may not be so simply expressed, but the vapor bubble, if it persists, would exhibit a vibratory response that propagates through the coolant as an acoustic signal. Sensitive microphones have the capability to measure the frequency and pressure amplitude of condensible and noncondensible bubble oscillations.

The free surface of a confined flow does not generate noise unless the surface has been disturbed by turbulence, eddies, waves, or bubbles. The acoustic characterization of the confined free surface flow associated with the reactor coolant system hot leg piping 18 may be empirically determined from model or full scale testing. A sensitive microphone may be sufficient for this purpose. During shutdown cooling, the existence of a free surface flow in the hot leg piping 18 is expected, and knowledge of the level of the free surface 31 is essential to preventing generation of a gas core in the exit vortex 30 to the shutdown cooling system. Although empirically determined acoustic characteristics of the turbulent coolant flow may be sufficient to interpret the level, the acoustic alteration of a sonic signal by reflection or transmission through the free surface 31 provides more definitive information for measurement of the level. Thus, the sensor assemblies 53, 54 in the FIG. 2 embodiment each use a sonic pulse or ultrasonic transmitter T1, T2 and a microphone receiver R1, R2 as the source of information necessary to characterize the fluid flow conditions.

The frequency of the important physical phenomena is mostly in the audible range. The emission frequencies of the transmitters T1, T2 are preferably selected to be most modified in frequency or phase by the physical phenomena. In the embodiment of FIG. 2, each sensor assembly 53, 54 has a single transmitter and receiver. However, it may be desirable to include a pair of transmitters and receivers for each sensor assembly to take advantage of the compressibility difference of the water and air at the air/water interface such that the level may be better interpreted. Furthermore, the orientations of the transmitters and receivers are shown in FIG. 2 to take advantage of the change in transmission through the interface at the free surface 31.

During shutdown cooling, the coolant flow is drawn from the hot leg 18. Since the hot leg pipe 18 is not completely filled with water, the air/water interface 31 forms, as shown in FIG. 2. At high water levels, eddies, without the presence of a vortex, may form in the upper end 28' of the drain pipe 28. These eddies have periodic shedding from the edge of the opening, which is an audible phenomena with a different frequency than the turbulent eddies 57 formed at low water levels which have a smaller length scale. Another flow possibility is the formation of a filled central vortex in the drain pipe 28. This causes an acceleration of the flow which will likely increase fluid shear with an accompanying increase in eddying and turbulence. This flow condition will have a different and unique acoustic signature. At reduced water levels, an air core will be present in the inlet vortex. This core may extend deep into the drain pipe 28 and break up with the resulting entrainment of air into the flow to the drain pump 33. Detection of these latter conditions is possible through the monitoring of bubble oscillations, the increase in turbulence activity, and/or the sensing of the core air/water interface as mentioned above.

Under extreme conditions, solid particulates 42 may enter the flow stream. Solid particles 42 in the flow will have still a different acoustic signature as a consequence of eddies occurring in front of the particles, particle-to-particle contact, and particle-to-metal contact.

Figure 3:
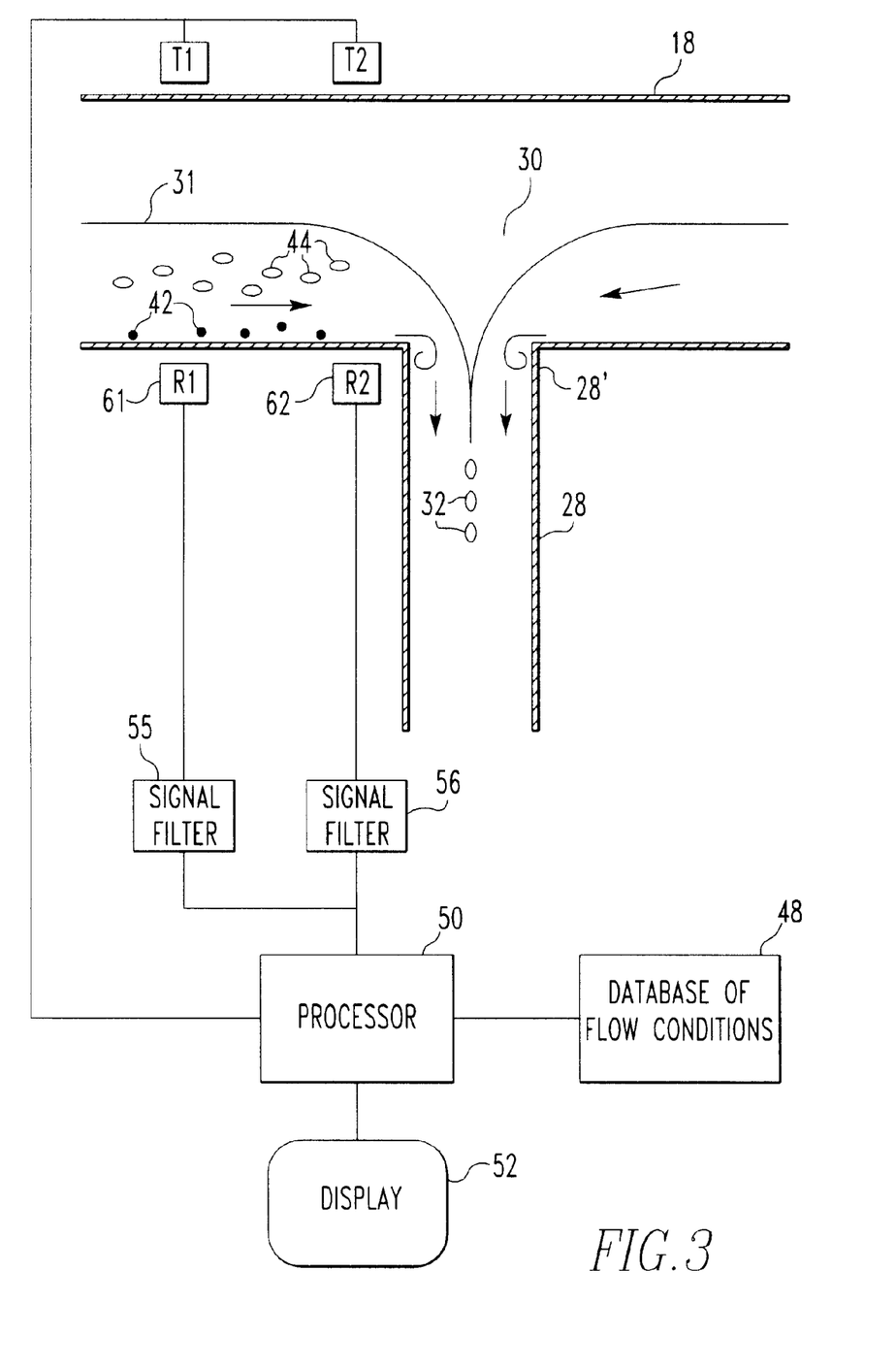
Fig. 3 is an enlarged, fragmented schematic view of the hot leg and drain pipe of FIG. 1 with a flow condition monitoring system according to another embodiment of the present invention attached.

An alternative embodiment of the flow condition monitor 60 of the present invention is shown in FIG. 3. The arrangement shown in FIG. 3 is similar to that shown in FIG. 2, except that the two sensor assemblies 61, 62 are both positioned upstream of the drain pipe opening 28'. This arrangement of sensor assemblies 61, 62 will detect somewhat different acoustic patterns than the arrangement shown in FIG. 2, but will otherwise operate in substantially the same manner. The arrangement shown in FIG. 3 can also be used to monitor flow conditions in a straight section of pipe remote from the drain pipe opening 28'.

Figure 4:
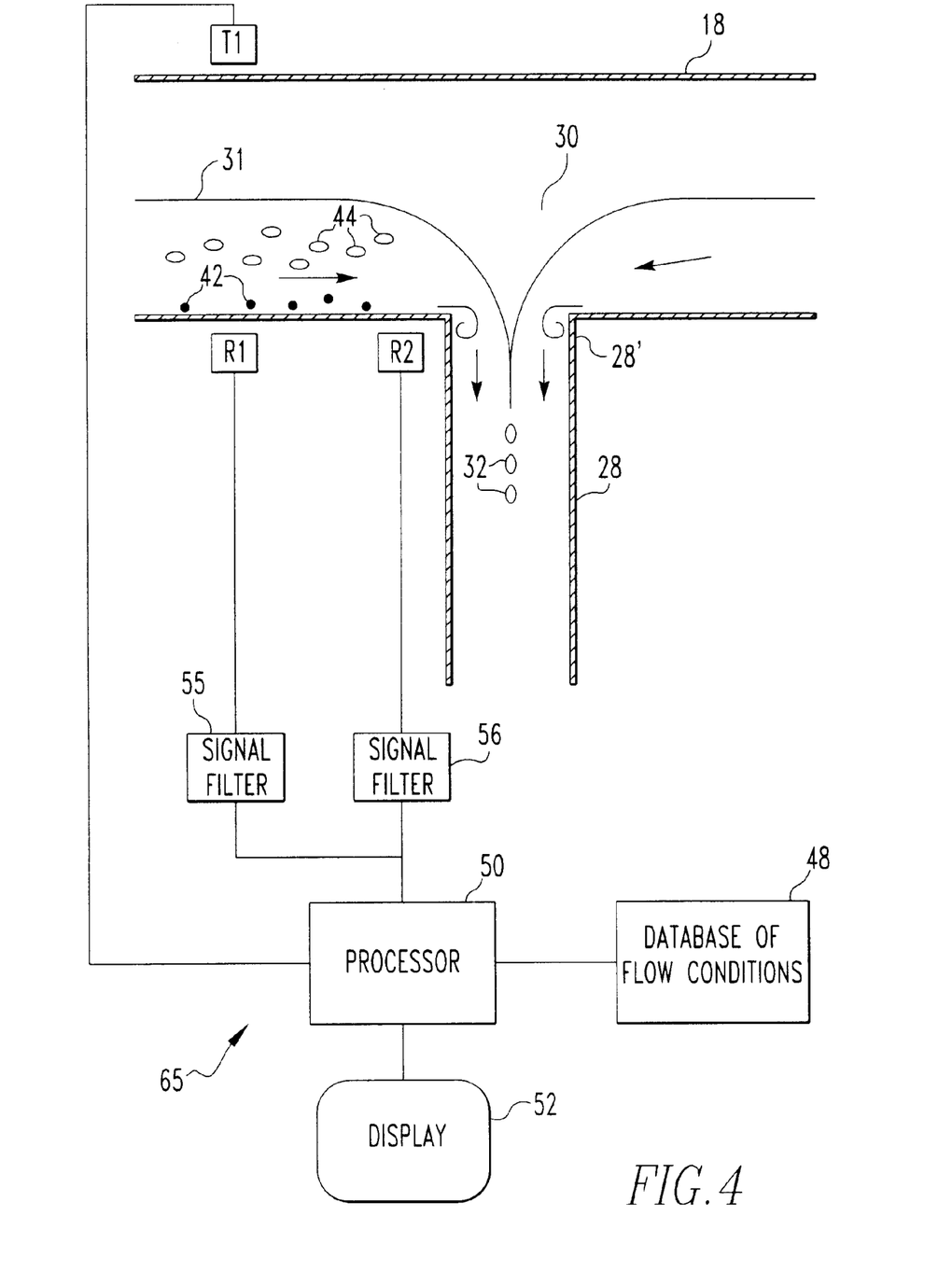
FIG. 4 is an enlarged, fragmented schematic view of the hot leg and drain pipe of FIG. 1 with a flow condition monitoring system according to another embodiment of the present invention attached.

Another alternative embodiment of the flow condition monitor 65 of the present invention is shown in FIG. 4. The arrangement shown in FIG. 4 is similar to that shown in FIG. 3, except that a single transmitter T1 provides an acoustic disturbance which is detected by both of the receivers R1, R2. The upstream receiver R1 provides information about the magnitude and frequency of the original disturbance, while the downstream receiver R2 determines how the disturbance attenuates with distance, thereby allowing the system to better determine where the acoustic disturbance is coming from.

Figure 5:
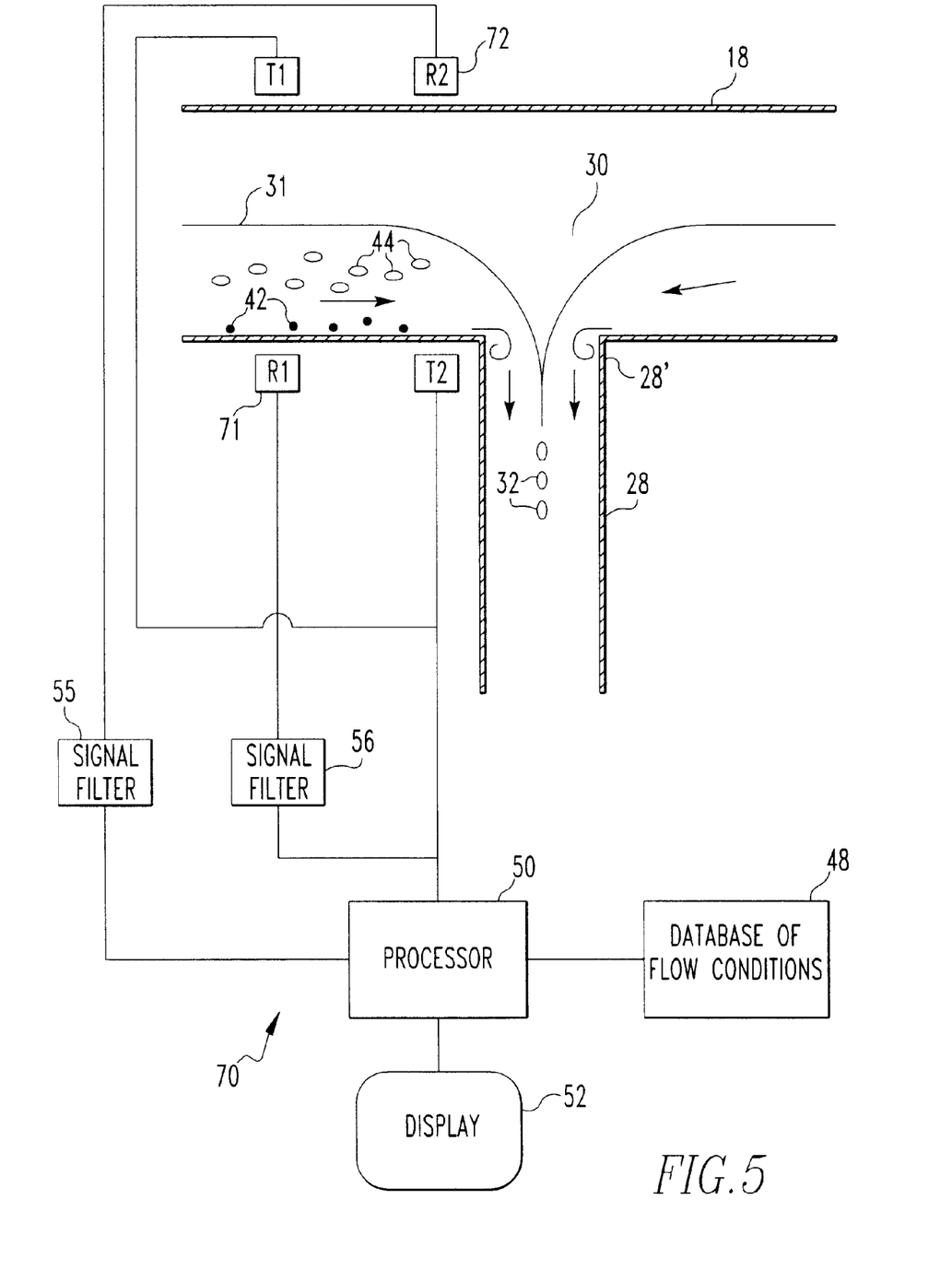
FIG. 5 is an enlarged, fragmented schematic view of the hot leg and drain pipe of FIG. 1 with a flow condition monitoring system according to another embodiment of the present invention attached.

Another alternative embodiment of the flow condition monitor 70 of the present invention is shown in FIG. 5. The arrangement shown in FIG. 5 is similar to that shown in FIG. 3, except that the transmitter T2 of the second sensor assembly 72 is placed on an opposite side of the pipe 18 from the transmitter T1 of the first sensor assembly 71. This arrangement will detect somewhat different acoustic patterns than the arrangement shown in FIG. 3, but will otherwise operate in substantially the same manner. The arrangement shown in FIG. 5 can also be used to monitor flow conditions in a straight section of pipe remote from the drain pipe opening 28'.

Figure 6:
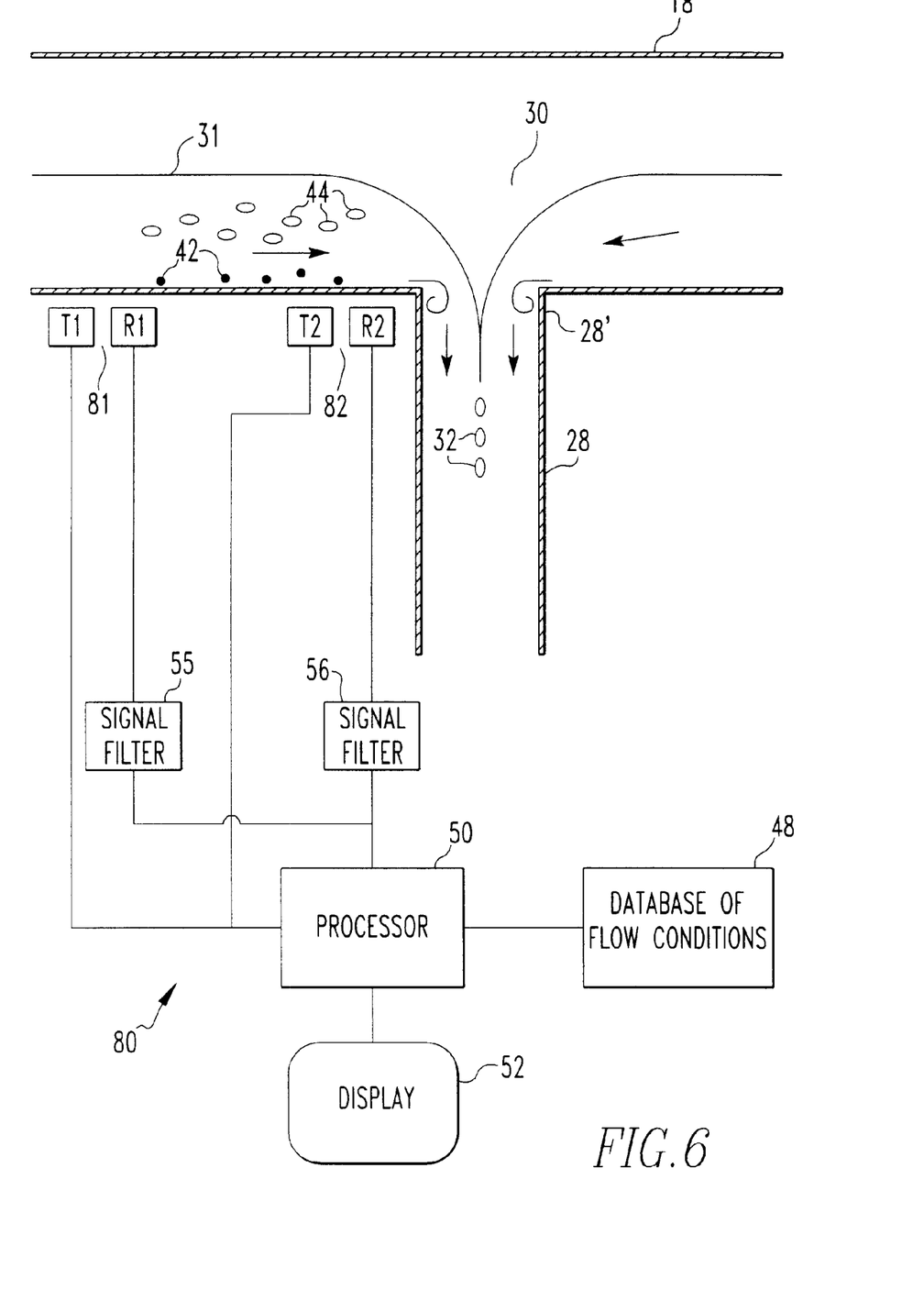
FIG. 6 is an enlarged, fragmented schematic view of the hot leg and drain pipe of FIG. 1 with a flow condition monitoring system according to another embodiment of the present invention attached.

Another alternative embodiment of the flow condition monitor 80 of the present invention is shown in FIG. 6. The arrangement shown in FIG. 6 is similar to that shown in FIG. 3, except that the transmitters T1, T2 of each sensor assembly 81, 82 are placed on the same side of the pipe 18 as the receivers R1, R2 of each sensor assembly 81, 82. This arrangement will provide better information in some circumstances by capturing the variation associated with reflection from the air/water interface at the free surface 31.

The acoustic sensor technology for the embodiments of the present invention described above is available commercially. So-called loose part monitors, which are typically located on the reactor vessel and steam generators, have sufficient sensitivity to listen to acoustic emissions from a reactor coolant pump. In addition, ultrasonic cross flow monitors apply the delay of the modification of an ultrasonic signal by turbulent eddies using pairs of transmitters/receivers mounted some distance apart to interpret the coolant flow rate.

Figure 7:
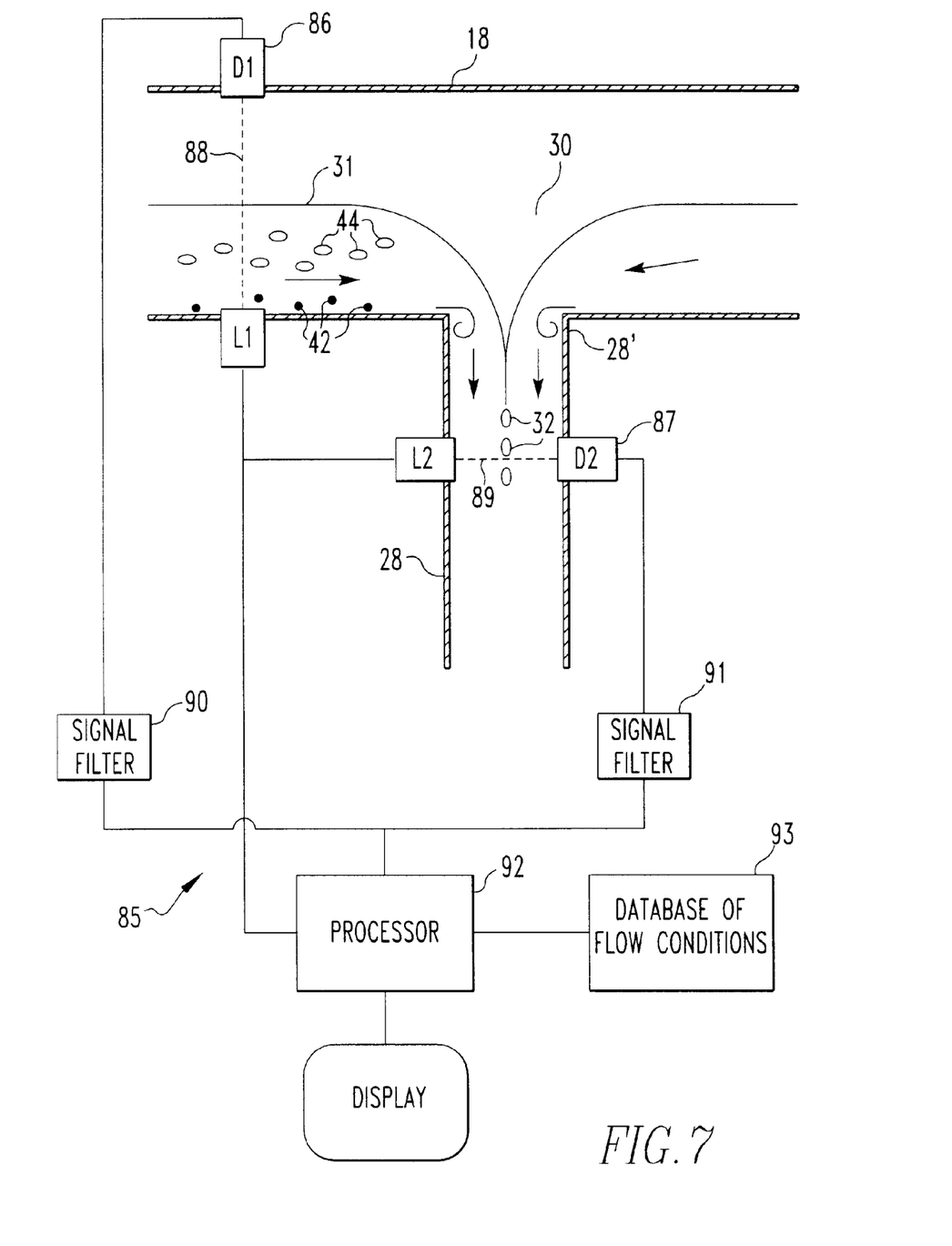
FIG. 7 is an enlarged, fragmented schematic view of the hot leg and drain pipe of FIG. 1 with a flow condition monitoring system according to another embodiment of the present invention attached.

Another alternative embodiment of the flow condition monitor 85 of the present invention is shown in FIG. 7. The arrangement shown in FIG. 7 is similar to that shown in FIG. 2, except that the sensor assemblies 86, 87 are laser/optical sensor assemblies. Each sensor assembly includes a laser beam source L1, L2 and a laser beam detector D1, D2. The laser beam source L1, L2 and detector D1, D2 components penetrate the main pipe 18 and the drain pipe 28 and cause respective laser beams 88, 89 to pass through the fluid flowing within the pipes 18, 28. The optical disruption patterns in the laser beam signals are filtered by signal filters 90, 91 and processed in much the same way as the acoustic patterns of the other types of sensor assemblies described above. The optical disruption patterns are processed by the processor 92 to compare and match the detected patterns with the predetermined patterns contained in the database 93 corresponding to known flow conditions. The determined flow conditions are then communicated to the nuclear plant operator using a video display 94 or other suitable communication means.

The flow condition monitor of the present invention has applications other than monitoring the coolant flow conditions in the drain pipe of a pressurized water reactor. For example, the sensor assemblies can be attached to the main pipe immediately downstream of the reactor to provide useful information about the condition of the reactor coolant flow following an accident situation. The flow condition monitor may also provide useful information in connection with the chemical volume control systems, the steam components on the secondary side of PWR reactors, and various fluid flow systems in boiling water reactors.

It will be appreciated that the present invention is not limited to the exact constructions that have been described above and illustrated in the accompanying drawings, and that various modifications and changes can be made without departing from the scope and spirit of the invention. It is intended that the scope of the invention only be limited by the appended claims.

What is claimed is:

1. A flow condition monitoring system for monitoring fluid flow conditions in a nuclear power plant, comprising:
   a first sensor assembly positioned near a fluid flow to be monitored, said sensor assembly having an output signal;
   a database containing known output signal characteristics of various fluid flow conditions being monitored; and
   a processor means connected to said first sensor assembly and to said database for receiving and comparing the signal from the sensor assembly with the known characteristics contained in the database to determine a condition of the fluid flow.

2. The flow condition monitoring system of claim 1, wherein said sensor assembly comprises an acoustic receiver for detecting acoustic characteristics of the fluid flow, and said database contains known acoustic characteristics of the various fluid flow conditions being monitored.

3. The flow condition monitoring system of claim 2, wherein said sensor assembly further comprises an acoustic transmitter positioned adjacent to the fluid flow to enhance the acoustic characteristics detected by said acoustic receiver.

4. The flow condition monitoring system of claim 3, wherein said transmitter and said receiver are positioned on opposite sides of the fluid flow from each other.

5. The flow condition monitoring system of claim 3, wherein said transmitter and said receiver are positioned on the same side of the fluid flow.

6. The flow condition monitoring system of claim 1, further comprising a second sensor assembly spaced from said first sensor assembly, said second sensor assembly having a second output signal, and said processor means compares said second output signal to said first output signal to determine a location of a disturbance detected by the first sensor assembly.

7. The flow condition monitoring system of claim 1, further comprising a filter connected between said sensor assembly and said processor for removing undesired noise from said output signal.

8. The flow condition monitoring system of claim 1, further comprising a display device connected to said processor means for communicating said determined fluid flow condition to a nuclear plant operator.

9. The flow condition monitoring system of claim 1, wherein said fluid flow conditions being monitored include the existence of entrained bubbles and solid particulates in the fluid flow.

10. The flow condition monitoring system of claim 9, wherein said fluid flow conditions being monitored further include a free surface and a vortex condition in the fluid flow.

11. A flow condition monitoring system for monitoring fluid flow conditions in a nuclear power plant comprising:

a first sensor assembly comprising a laser beam transmitter and receiver for detecting optical characteristics in the fluid flow, and a database containing known optical characteristics of the various fluid flow conditions being monitored; and a processor means connected to said first sensor assembly and to said database for receiving and comparing the signal from the sensor assembly with the known characteristics contained in the database to determine a condition of the fluid flow.

12. A flow condition monitoring system for monitoring the coolant flow in a shutdown cooling system drain pump of a nuclear power plant during midloop operation, comprising:

a main pipe to conduct coolant from a nuclear reactor to a steam generator, said main pipe being substantially horizontal and having an upper region and a lower region;

a drain pipe connected at the lower region of the main pipe to conduct coolant from the lower region to a drain pump;

a first sensor assembly positioned near the drain pipe for detecting acoustic signals from a coolant flow within the drain pipe;

a database of known acoustic signal characteristics of various flow conditions being monitored; and a processor that compares the detected acoustic signals with the known acoustic characteristics contained in the database to identify a coolant flow condition.

13. The flow condition monitoring system of claim 12, wherein said first sensor assembly comprises an acoustic signal transmitter to enhance the acoustic signals detected by said acoustic receiver.

14. The flow condition monitoring system of claim 12, wherein said transmitter and said receiver are positioned on opposite sides of the drain pipe from each other.

15. The flow condition monitoring system of claim 12, further comprising a second sensor assembly for detecting acoustic signals from the coolant flow within the drain pipe, said second sensor assembly being spaced from said first sensor assembly, and said processor comprising a means for comparing the detected acoustic signals from said second sensor assembly to the detected acoustic signals from said first sensor assembly to assist identification of the flow condition by monitoring the variation or attenuation of the signals in time and distance.

16. The flow condition monitoring system of claim 12, wherein said fluid flow conditions being monitored include the existence of entrained bubbles and solid particulates in the fluid flow.

17. The flow condition monitoring system of claim 16, wherein said fluid flow conditions being monitored further include a free surface and a vortex condition in the fluid flow.

18. A method of monitoring flow conditions in a nuclear power plant, comprising the steps of:

positioning a first sensor assembly near a fluid flow to be monitored;

generating a first output signal by said first sensor assembly indicative of a fluid flow condition;

providing a database containing known output signal characteristics of various fluid flow conditions being monitored; and comparing said first output signal with the known characteristics of various fluid flow conditions to identify the fluid flow condition.

19. The method of monitoring flow conditions according to claim 18, wherein the plant includes a main pipe to conduct coolant from a nuclear reactor to a steam generator, said main pipe being substantially horizontal and having an upper region and a lower region with a drain pipe connected at the lower region of the main pipe to conduct coolant from the lower region to a drain pump, and said positioning step comprises positioning the first sensor assembly near an intersection of said drain pipe and said main pipe.

20. The method of monitoring flow conditions according to claim 19, further comprising the step of adjusting a coolant flow level in response to the identified fluid flow condition.

21. The method of monitoring flow conditions according to claim 18, wherein said sensor assembly comprises an acoustic receiver, and said generating step comprises generating a first output signal by said first sensor assembly based on an acoustic pattern emanating from the fluid flow.

22. The method of monitoring flow conditions according to claim 21, further comprising the step of placing an acoustic transmitter near the fluid flow and transmitting ultrasonic signals to enhance the acoustic patterns detected by said acoustic receiver.

23. The method of monitoring flow conditions according to claim 18, further comprising the steps of:

positioning a second sensor assembly near the fluid flow to be monitored;

generating a second output signal by said second sensor-assembly; and comparing said second output signal to said first output signal assist identification of the flow condition by monitoring the variation of the signals in time and distance.

24. The method of monitoring flow conditions according to claim 18, wherein said fluid flow conditions being monitored include the existence of entrained bubbles and solid particulates in the fluid flow.

25. The method of monitoring flow conditions according to claim 24, wherein said fluid flow conditions being monitored further include a free surface and a vortex condition in the fluid flow.

* * * * *